United States Patent [19]

Metzger et al.

[11] Patent Number: 4,859,605
[45] Date of Patent: Aug. 22, 1989

[54] PROCESS FOR PREPARATION OF SAMPLES FOR ANALYSIS

[75] Inventors: Andre Metzger, Le Verger, France; Peter Grimm, Frenkendork, Switzerland; Andre J. Nohl, Menlo Park; Vance J. Nau, Cupertino, both of Calif.

[73] Assignee: Ciba-Geigy Corporation, Ardsley, N.Y.

[21] Appl. No.: 942,353

[22] Filed: Dec. 16, 1986

[51] Int. Cl.$^4$ .......................... G01N 1/10; G01N 1/28
[52] U.S. Cl. ......................................... 436/43; 436/54; 436/174; 436/179; 436/180
[58] Field of Search ........................ 436/43, 47, 48, 52, 436/53, 54, 174, 179, 180; 73/864.22

[56] References Cited

U.S. PATENT DOCUMENTS

| | | | |
|---|---|---|---|
| 3,223,348 | 5/1965 | Ferrari et al. | |
| 3,223,486 | 12/1965 | Holl et al. | 436/52 X |
| 3,536,449 | 10/1970 | Astle | 436/179 |
| 3,836,329 | 9/1974 | Jordan | 436/49 |
| 3,843,323 | 10/1978 | Quame | 422/65 X |
| 3,883,305 | 5/1975 | Hoskins et al. | 422/65 |
| 3,990,853 | 11/1976 | Godin | 422/103 X |
| 3,994,687 | 11/1976 | Engelbrecht | 436/179 X |
| 4,002,053 | 1/1977 | Hayakawa | 73/32 R |
| 4,009,998 | 3/1977 | Benningfield | 436/52 X |
| 4,030,888 | 6/1977 | Yamamoto et al. | 436/43 X |
| 4,036,590 | 7/1977 | Helder et al. | 436/43 |
| 4,130,394 | 12/1978 | Negersmith | 436/179 |
| 4,181,009 | 1/1980 | Williamson | 73/61.4 |
| 4,526,754 | 7/1985 | Burns et al. | 436/53 X |
| 4,562,044 | 12/1985 | Bohl | 422/65 X |
| 4,746,491 | 5/1988 | Ohlin | 436/54 X |

FOREIGN PATENT DOCUMENTS

| | | |
|---|---|---|
| 0089937 | 9/1983 | European Pat. Off. |
| 2579749 | 10/1986 | France |
| 0187863 | 9/1985 | Japan ...................................... 436/43 |

OTHER PUBLICATIONS

Messan Von Stoffspezifischen Groben in der Chemischen Produktion Erfahrungen, Trends, by Altermatt et al., 9/1986.

An Apparatus for Sample Preparation in a Measurement and/or Control System and the Application of this Apparatus, Priority: Swiss, Aug. 29, 1986, Ciba-Geigy AG, Case 7-16068/CIT, 29 pages.

Primary Examiner—Robert J. Hill, Jr.
Attorney, Agent, or Firm—Irell & Manella

[57] ABSTRACT

An automated sample preparation system for chemical assay of samples of materials. The sample preparation system includes a sample preparation chamber which includes a removable cup for taking solid or very viscous samples to the sample preparation system. The cup may be attached in sealing relationship to a cap through which extends various utilities such as a mixer/grinder to grind solid samples and mix non-homogenous samples, a fill pipe to pump in liquid samples, an effluent pipe in the sump of the cap to allow pumping of samples and solvents and a nozzle to allow liquids to be sprayed against the walls. A sample metering valve associated with the sample preparation chamber allows a know volume of sample to be isolated so that solvent may be pumped in to dilute the sample to a user defined concentration. A reversible pump is coupled by a pair of manifolds which are themselves coupled by solenoid operated valves to various sources of solvents, pressurized gas, vacuum, water, the sample preparation chamber and the assay system. A control system coordinates the operation of all remotely controllable units in the system to allow the user to customize various ample preparation processes.

14 Claims, 5 Drawing Sheets

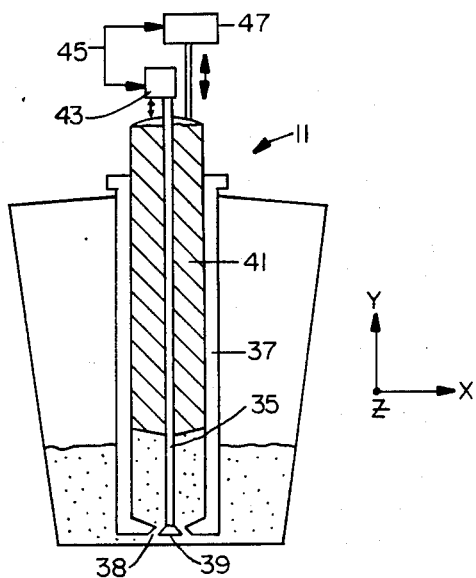
FIG. 4
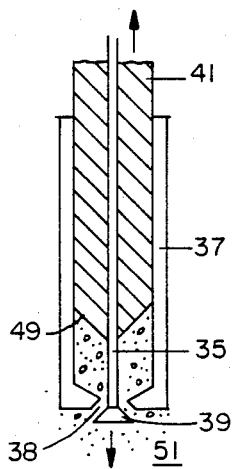   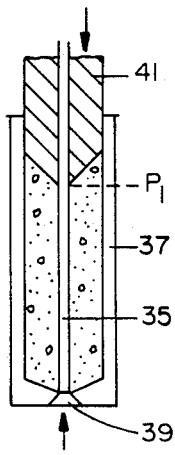   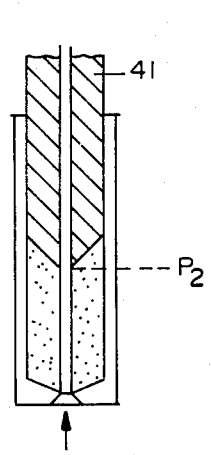   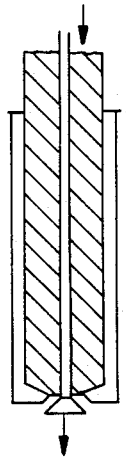
FIG. 5    FIG. 6    FIG. 7    FIG. 8

PROCESS FOR PREPARATION OF SAMPLES FOR ANALYSIS

BACKGROUND OF THE INVENTION

The invention pertains to the field of sample preparation systems for automated chemical analysis. More, particularly, the invention relates to the field of systems for processing liquid, solid or slurry samples for analysis by liquid chromatography systems.

In many chemical processing plants or laboratories, there is a need for chemical assays for determining the components and/or proportions of the chemical material being dealt with or made. Often this is done using a liquid chromatography system (hereafter liquid chromatography will be referred to as LC). To be suitable for analysis by liquid chromatography, the sample or sample solution must be homogenous, dissolved in an appropriate solvent, and of known concentration (if diluted).

The types of samples which must be dealt with are often quite varied, and often the manner of isolating an aliquot of sample to analyze is quite varied. For example, the sample preparation system may be called upon to prepare samples that are non-homogeneous, two phase, liquid/liquid or liquid/solid samples or slurries with entrained gas bubbles or foam. Further, the sample may be solid in either granulated, powder or tablet form. Some samples may be quite viscous while others are quite thin. Some samples may need to be taken from vats or tanks where they are stored or prepared while other samples may need to be taken from a process stream. Some samples are susceptible to pumping into the sample preparation system while other samples are solid or too viscous to pump and must be physically picked up by an operator of the sample preparation system.

Often it is necessary to dilute samples with solvents before pumping them through an LC column. Very precise control of the sample concentration is necessary in this case. To obtain this precise control, there must be some way to isolate a known volume of sample from the rest of the sample and to release it into a known quantity of diluent.

Prior art sample preparation systems have, to date, not been capable of handling all the above noted situations gracefully. Generally, prior art sample preparation systems are capable of handling only one type of sample, and major modifications or use of an entirely different system is needed to handle a different type of sample.

Thus there has arisen a need for a single sample preparation system which can easily and conveniently handle all the different types of samples which may be necessary to analyze.

SUMMARY OF THE INVENTION

In accordance with the teachings of the invention, there is provided a sample preparation system which can handle samples of the liquid, solid or slurry type. The system includes a sample preparation chamber having a removable cup which may be taken to the location of solid or extremely viscous samples and a measured amount of sample may be placed therein. The cup has a sloped bottom with a sump point or region which is lower than all other regions of the bottom. The cup attaches in any known, sealing manner to a cap. Through the cap are a fill/empty pipe through which the cup may be filled by pumping in liquid sample, solvent or diluent. The fill/empty pipe outlet is at or near the lowest point of the bottom, so the cup may also be emptied through this fill/empty pipe.

A solenoid operated or pneumatically operated sample metering valve is also provided with an inlet in the cup to allow a known volume of sample to be isolated from the rest of the sample. A nozzle is provided also whereby the walls of the cup may be washed down by pumping of solvent into the cup through the nozzle which deflects the solvent against the walls of the cup. After all excess sample and solvent has been pumped out of the cup, the isolated aliquot of sample may be released back into the cup, and a known volume of diluent may be pumped in to dilute the sample to the desired concentration.

For non-homogeneous samples or solid samples which must be ground into smaller particles prior to being dissolved, a mixer/grinder is provided. This device includes a drive apparatus for imparting rotational motion to a shaft which is connected to a propeller/grinder which is located in the cup.

For some applications, other mixers such as ultrasonic mixers similar to the one distributed by Sonics and Materials in Danbury, Connecticut, or a high speed homogenizer similar to the one distributed by Brinkman in Westbury, New York may be substituted. In some applications, use of these alternate mixers would be preferred.

An electrically or pneumatically driven reversible pump mechanism which is capable of accurate, repeatable delivery of user specified volumes of liquid provides the facility to move liquids into and out of the cup and to pump them to the injection port of a system. The pump is coupled through two solenoid operated valves to two manifolds. The inlet and outlet manifolds are merely a collection of valves configured to accomplish a desired task or series of tasks. These tasks may include dilution, extraction, sampling, solid phase extraction, low pressure chromatography and others, and may be connected to a variety of other equipment. These include the LC or other analyzer, the effluent (waste) line, several sources of different solvents, a source of pressure, a source of subatmospheric pressure, a water supply, an electrically or pneumatically driven six way valve for bringing in liquid or slurry sample from a vat or storage tank, the nozzle in the cup and a sample valve in a process stream. The process stream sample valve is also coupled to the effluent line through a two way solenoid operated or pneumatically driven valve.

A control circuit or system is coupled to the solenoid operated valves, the pump, the six way valve, the two way valve, the sample metering valve and the mixer/grinder drive mechanism. The control circuit implements a user interface by which the user may specify the operations to be performed by the system, and the parameters for the process to be performed. The control system then issues the proper control signals to the various elements in the system in the proper sequence to cause the desired sample preparation process to occur.

BRIEF DESCRIPTION OF THE DRAWINGS

FIG. 4 is a cross sectional view of another type of sample metering valve for handling slurries or other samples with gas bubbles therein which must be compressed.

FIGS. 5 through 8 are views of the sample metering valve of FIG. 4 in various states of its operation of drawing sample liquid, compressing any entrained gas, and determining the final, compressed volume.

DETAILED DESCRIPTION OF THE PREFERRED EMBODIMENT

Figure 1:
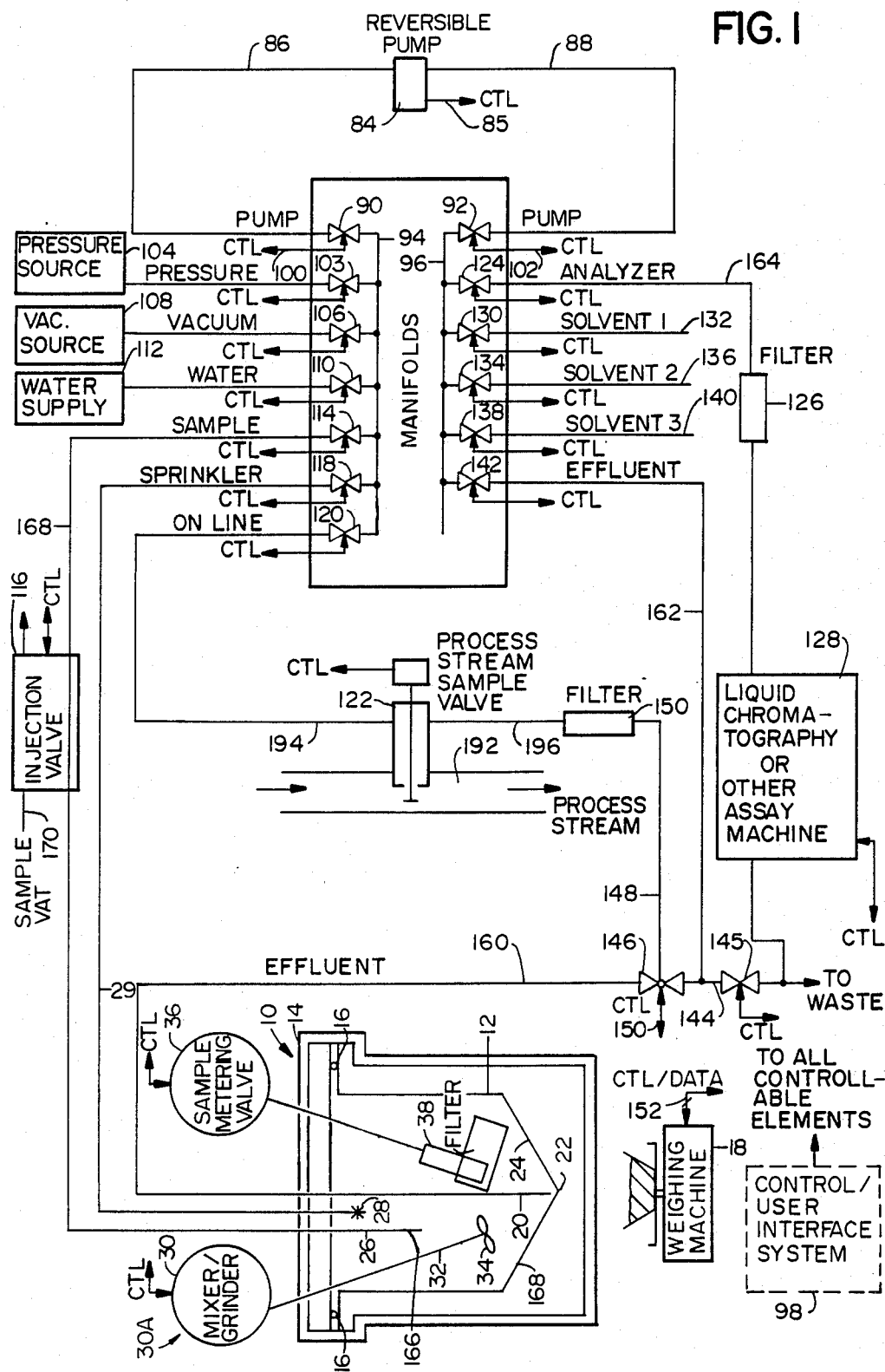
FIG. 1 is a diagram of the system of the invention.

Referring to FIG. 1 there is shown a diagram of the sample preparation system of the invention. The system includes a sample preparation chamber 10 the details of which are given in U.S. Patent application "Sample Preparation Chamber With Mixer/Grinder and Sample Aliquot Isolation", Serial Number 942,198, filed 12/16/86 which is hereby incorporated by reference. For completeness here, a short summary of its structure and operation will be given.

The sample preparation chamber is capable of being used to prepare many different types of samples for chemical assay, especially by liquid chromatography. The sample preparation chamber is comprised of a sloped bottom cup 12 which is lightweight, transparent and disposable for holding the sample liquid or solid. The cup threads or otherwise attaches to a cap 14 which serves to keep liquids in by a liquid seal 16 between the cup flange and the mating cap flange. The detachability of the cup allows the cup to be removed and taken to the location of the sample so that a measured amount of sample may be placed therein for solid samples which cannot be pumped as symbolized by the weighing machine 18. Several elements pass through the cap. These elements include a fill/drain pipe 20 which extends to the lowest point 22 in the sloped bottom 24 of the cup and has a diameter which is large enough to pump viscous liquids through without excessive pressure being required. A second fill pipe 26 also passes through the cap, but does not extend to the bottom of the cup. In the preferred embodiment, the fill pipe 26 is adjustable such that the height of the bottom of the fill pipe from the bottom of the cup 12 may be either manually adjusted or adjusted by any known mechanism acting under the control of the control system 98. This fill pipe may have a smaller inside diameter than the fill/empty pipe 20, and may be used to pump liquid sample, solvents or diluent into the cup, especially less viscous liquid samples.

There is also a nozzle 28 which extends through the cap 14. This nozzle is used to wash down the side walls of the cup 12. The nozzle 28 is a propeller like structure in line with the outlet of a pipe 29. To use this feature, the user pumps solvent or some other liquid through the pipe 29 connected to the nozzle. The fluid flow causes the propeller or nozzle element to spin. This deflects fluid laterally out toward the side walls of the cup 12 thereby washing down the walls.

The sample container also includes a mixer/grinder mechanism 30A. This mechanism includes a motor 30 driving a shaft 32 which passes through the cap 14. The shaft 32 is coupled to a propeller 34 or other stirring structure which may or may not be suitable for grinding solid samples. The user may change the structure of the mixer/grinder propeller 34 to best suit the types of samples the user customarily prepares for assay. For example, high speed homogenizers or ultrasonic probes may be substituted.

A sample metering valve 36 is also provided for allowing the user to isolate a known volume of sample from the rest of the material in the cup. In the particular embodiment shown in FIG. 1, the sample volume is isolated in the portion 38 of the sample metering valve. This known volume may then be released back into the cup 12 after the rest of the sample has been pumped to waste through an effluent line 20. The sample metering valve 36 and the mixer/grinder 30A may both be driven either by an electrical motor or a pneumatic drive mechanism. Those skilled in the art will appreciate an adequate drive mechanism for the mixer/grinder 30. The details of the sample metering valve are given in U.S. Patent application "Sample Valve For a Sample Preparation System", filed 12/16/86, Ser. No. 942,201 which is hereby incorporated by reference. For completeness here, a short summary of the different types of sample valves will be given.

Figure 2:
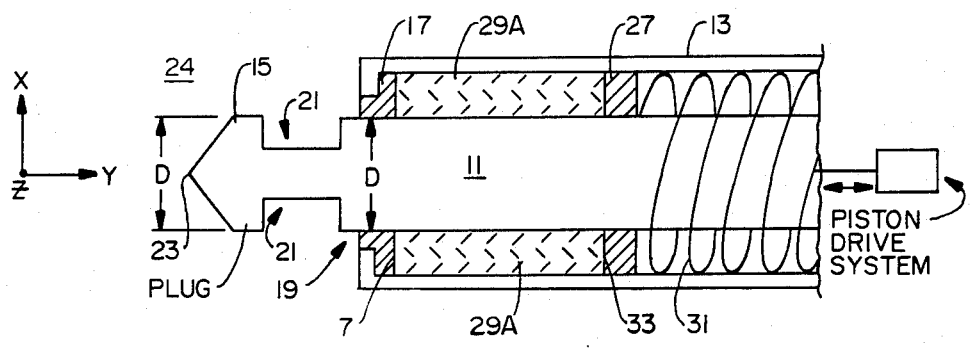
FIG. 2 is a cross sectional view of one type of sample metering valve of the invention with its piston extended.

The sample metering valve is shown in the extended position in FIG. 2. This valve is a device which can repeatedly and accurately isolate a known volume of sample from a larger volume of sample. The sample metering valve used in the invention includes an open end cylinder 13 in which there is positioned a piston 11 having a T shaped sealing end plug 15 having a tip 23. The piston 11 slides back and forth in the cylinder 13 within the confines of retaining rings 17,27 and material 29A between an extended position (indicated by the numeral 24) and a retracted position. The T shaped sealing end plug 15 is sized so as to form a sealing plug in the open end 19 of the cylinder. A cylindrical recess 21 is formed in the piston 11 up from the sealing plug end 15 and is placed on the piston 11 such that the recess 21 is exposed to the surrounding medium when the piston 11 is in the extended position. This causes the recess 21 to fill up with the material of the surrounding medium when the piston 11 is extended. When the piston 11 is retracted, the material in the recess 21 is isolated.

No O ring seals are used on the piston 11 in the valve of the invention. Instead, a soft material 29A is sandwiched at both ends 7 and 33 between two harder retaining rings 17 and 27. A spring 31 is disposed inside the cylinder concentrically around the piston 11. This spring 31 contacts the ring 27 of relatively harder material at the end farthest from the sealing plug 15 on the piston 11. The purpose of the spring 31 is to apply a bias force along the negative y axis to the relatively harder ring to exert pressure on the softer material 29A, which in the preferred embodiment is a sealing cylinder, to cause it to expand against the side wall of the piston 11 thereby forming a better seal. Because there are no gaps between the relatively harder sealing rings 17 and 27 and the relatively softer sealing cylinder 29A, and because the intersections between the rings 17 and 27 are not exposed to the surrounding medium when the piston 11 is extended, no dead volume is available to fill with unknown volumes of sample.

Typically, the piston 11 is driven either by a pneumatic system or by stepper motors (not shown).

Another embodiment of a metering sample valve is a syringe type valve shown in FIGS. 4 through 8. This valve is especially useful in dealing with slurries with entrained gas bubbles or foam. These bubbles of gas take up volume in an isolated sample which can lead to inaccuracy in predicting the actual volume of liquid which has been isolated in a metering valve. The syringe tube sample metering valve 11 utilizes a cylinder 37 with a piston 41 therein and a separately movable end plug or valve 39. The end plug 39 is moved to an open position so that the surrounding medium 51 may enter the cylinder 37 through an opening 38. During filling of the valve, the piston 41 is drawn by a piston drive mechanism 47 to the piston's retracted position to create more volume inside the cylinder 37 thereby lowering the pressure inside the cylinder and causing the it to fill with sample. After the cylinder sample volume is filled, the valve 39 is closed and the piston 41 is separately moved down toward the valve 39 thereby compressing any gas bubbles entrained in or otherwise trapped in the sample volume of the cylinder 37. During this downward movement of the piston 41, the amount of movement, i.e., the distance the piston 41 moves toward the valve during the compression stroke, is monitored by a sensor (not shown but part of the piston drive mechanism 47). When the piston has moved far enough to satisfy a user defined criteria, such as spill from the valve 39 caused by the the compression pressure slightly exceeding the force with which the valve 39 is held closed by the valve drive mechanism 43, the total movement of the piston 41 is determined. This done by direct measurement, interpolation of sensor output data from the sensor or by reading the motor step number in the case of a stepper motor drive 47 for the piston 41. The total volume of liquid in the syringe valve 11 is calculated by subtracting the volume displaced by the movement of the piston toward the valve 39 during the compression stroke from the total original volume of sample in the cylinder before the beginning of movement of the piston during the compression stroke.

The sample may then be released by causing the valve 39 to unseal the cylinder and either letting the sample flow out of the cylinder 37 or by pushing it out by further movement of the piston 41. With liquid samples, especially very viscous samples, the syringe type embodiment has the added advantage that the process of filling the cylinder sample volume with sample may be speeded up by using the piston to draw up the sample into the cylinder by moving it away from the sealing plug from a position adjacent to the sealing plug at the time the plug is opened.

Figure 9:
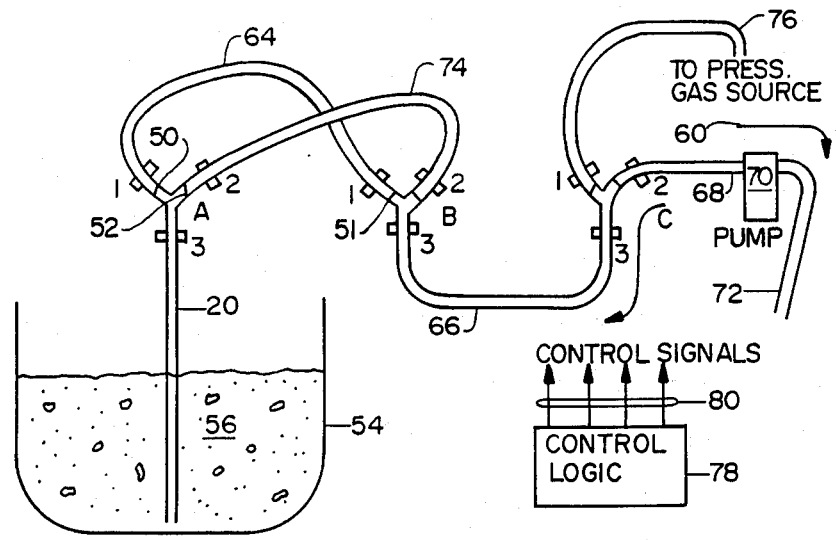
FIG. 9 is a diagram of another type of sample metering valve suitable for sampling slurries.

The preferred embodiment of the sample metering valve for use in slurry and other sample situations where the volume consumed by gas bubbles exists is comprised of three, three way valves coupled to a sample metering pump and a source of pressurization (gas in this example) as shown in FIG. 9. A first three way valve A (basically a Y valve) has its common port 3 coupled to a fill pipe 20 in a sample chamber 54. The number 1 port of valve A is coupled to the number 1 port of another three way valve B. This connection forms a sample chamber 64 between the valve mechanisms of the first and second valves, A and B respectively. The number 2 ports of the two valves A and B are coupled together to form a bypass loop 74. The common port 3 of the second valve B is coupled to the common port 3 of a third three way valve C which has one of its ports, port 2, coupled to the sample pump 70 and the other port, port 1, coupled to the source of pressurized gas at source pipe 76.

The valves A, B and C are operated to couple the sampling pump 70 to the fill tube 20 in the chamber. The sample pump is driven so as to suck sample up through the fill tube 20 into the first valve A and out through the sample chamber 64 until enough sample is drawn to completely fill the sample chamber 64 and excess sample is drawn through the valve B into pipe 66 which excess sample is sufficient in volume to compensate for the effects of compression. The first valve A number 1 port is then closed by turning its valve plate 50 to isolate the sample in the sample chamber 64, and the third valve C is operated to couple the pressurized gas at source pipe 76 into the sample chamber 64 through the B valve so as to compress the gas bubbles in the sample trapped there to a small volume. The second valve B is then operated to trap the compressed sample between the first and second valving plates 50 and 51 in valves A and B respectively. This trapped volume may be a known volume or an unknown volume of high reproducibility depending on the application. The sample pump 70 is then operated in the direction so as to empty the rest of the sample 56 not so trapped through the lines 74 and 66. This empties these lines and the sample chamber and prepares the system to be cleaned out with solvent. The solvent is then pumped in through the same lines to fill the container 54 and rinse excess sample away. The solvent is then pumped to waste. Alternatively, the pump 70 may substitute for the compressed gas at source pipe 76, or a pressurized sealed head space may substitute as the sample drive mechanism for the pump 70 in the withdrawal of sample 56 from vessel 54 either through loops 74 or 64. The valves and pump are then operated so as to free the trapped sample in sample chamber 64 and to pump a known quantity of solvent through the lines and to push the trapped sample into the vessel 54 in preparation for the next desired sample preparation step.

Referring again to FIG. 1, the rest of the sample preparation system will be described. A key element in the system is the liquid pump 84. This pump is reversible such that it may pump liquid in either direction though the pipes 86 and 88 which are coupled to the pump's input and output ports. The pump 84 must be capable of delivering repeatedly, very accurate volumes of liquid since it will be used to pump in precise volumes of diluent to dilute the known volume of sample released from the sample metering valve. Typically pumps with inlet and outlet check valve structures are not reproducible enough in the deliveries of known volumes because of the dead volume of liquid which inevitably results from the check valve operation. Any type of pump with an unpredictable or not reproducible dead volume associated with its output valve structure will not be satisfactory. Dead volume is the unknown, variable volume of liquid trapped by the output valve mechanism which will be released the next time the valve opens to thereby destroy the accuracy of the volume delivered by the pump. Any type of pump and valve/flow meter combination which can accurately deliver a user defined volume of diluent will be satisfactory. A positive displacement pump which is accurate to within 1% volumetric accuracy and 1% relative standard deviation in dispensement precision will be adequate. One type of pump which works well is a "swash" pump. This type, as is known by those skilled in the art, uses a tilted rotating shaft inside a cylinder. The walls of the cylinder have input and output ports located on opposite sides at different levels such that the rotation of the shaft opens and closes the ports sequentially. The axial displacement of the shaft within the cylinder causes liquid to be drawn in from one port and pumped out the other port. The direction of pumping may be changed by reversing the direction of rotation of the pumping plate. The rotation of the plate is controlled by a stepper motor or other mechanism which can precisely control the position of the plate to maintain the output port closed when pumping is not occurring. Such pumps are a manufactured by Fluid Metering Inc. and are patented in U.S. Pat. Nos. 3,168,872 and 3,257,953 both of which are hereby incorporated by reference. Other types of pumps such as syringe pumps will also suffice to practice the invention, but in high volume applications, these syringe pumps may not be commercially practicable.

Another important criteria regarding the selection of the pump is that the sealing mechanism be reliable for a large number of cycles without failure.

The pump 84 is coupled by a control bus 85 to a control circuit/user interface 98 which provides control signals to cause the pump 84 to pump an amount of liquid defined by the control signal in the direction defined by the control signal. The pump drive mechanism may be any type of mechanism such as pneumatic, or stepper motor which can provide the necessary precision of rotor position and accuracy in delivery volume. The details of the control circuit/user interface are not critical to the invention, and those skilled in the art will appreciate that many different type of control mechanisms may be used to control the pumps and valves in the system to do a plurality of different functions and to prepare a plurality of different types of samples for analysis. For example, a programmed digital computer driving stepper motor interface circuits and interface circuits for solenoid operated valves may be used. Further, the control circuit may be dedicated logic, a state machine or a mechanical or analog electronic computer. The interface to the pump and valves may also be via electrically driven pneumatic or hydraulic valves which send pneumatic or hydraulic signals to the pump and valves in the system to cause them to perform the desired functions in the proper sequence. Further, the control circuit 98 may not be a circuit at all in some embodiments, but instead may be a human operator who does all the calculations and operates the valves in accordance with the sequence of steps necessary to process a particular type of sample.

The pipes 86 and 88 are coupled, respectively, through valves 90 and 92 to manifolds 94 and 96. All valves, like the pump 84, are coupled by control signals to a control circuit/user interface 98. The control signals are not shown in full detail since to do so would unduly complicate the drawing. All valves may be solenoid operated valves, or they may be pneumatically operated or driven by stepper motors. The manner of driving the valves is not critical to the invention. Regardless of the type of drive mechanism, all valves should be such that they may be opened and closed upon receipt of the proper control signal from whatever control mechanism is being used to control the system. For example, these control signals arrive on control buses 100 and 102 for valves 90 and 92, respectively.

The manifolds 94 and 96 are coupled through a plurality of valves to a variety of sources of inputs and to a variety of destinations or devices. For example, valve 103 couples a pressure source 104 to the manifold 94. The other valves and facilities in the system are: valve 106 which couples the vacuum source 108 to the manifold 94; valve 110 which couples water supply 112 to the manifold 94; valve 114 which couples the manifold 94 to a 6 way injection valve and to the fill pipe 26; valve 118 couples the manifold 94 to the nozzle 28; valve 120 which couples manifold 94 to an isolation chamber (not shown) in the process stream sample valve 122; valve 124 which couples the manifold 96 to a filter 126 and an analyzer 128; valve 130 which couples manifold 96 to an input port 132 for a first solvent; valve 134 which couples the manifold 96 to an input port 136 for a second type of solvent; valve 138 which couples the manifold 96 to an input port 140 for a third type of solvent; valve 142 which couples the manifold 96 to an effluent pipe 144 which is coupled to the fill/empty pipe 20 through a three way valve 146. The three way valve 146 has an input port 148 which is coupled through a filter 150 to the isolation chamber of the process stream sample valve 122. The three way valve 146 also has two output ports one of which is the fill/empty pipe 20 and the other of which is the effluent line 144. A control signal on the control bus 150 controls which of the output ports of the valve 146 at any particular time is coupled to the input port 148. Each of the valves coupled to the manifolds 94 and 96 is capable of being controlled by the control circuit/user interface circuit 98 such that a control signal from the user interface may open or close each valve.

THE PROCESSES FOR SAMPLE PREPARATION

Solid and Very Viscous Samples Which Cannot be Pumped

The system described above is capable of preparing in different ways many different types of samples from several different sources for analysis by the analyzer 128. For example, the system provides the facility to convert solid samples to diluted liquids at a known concentration. This process involves the following steps. For tablet or granular samples or viscous liquids which do not readily flow, the cup 12 is removed from the cap 14 and taken to the location of the sample. A user determined quantity of the sample is placed in the cup. This may be done by using the weighing machine 18 to weigh the cup before and after placing the sample therein to determine the mass of the sample which has been placed in the cup. The weighing machine 18 can be used to transmit the weight data directly to the control circuit 98 via the bus 152. The control circuit 98 may then use this information to perform calculations to adjust the dilution factors appropriately, or simply retransmit such information to another device.

The cup is then placed back on the cap 14. If the sample is a tablet, the control circuit 98 turns on the mixer/grinder 30A to grind the tablet into smaller pieces to speed up the process of dissolving it in diluent. For granulated or viscous samples, this step may be eliminated.

Next, the sample must be dissolved to form a solution of the proper viscosity, composition, and concentration for pumping through the LC column 128 or other analyzer. Because the control apparatus 98 knows the weight of the sample in the cup from previous steps and has the desired concentration from the user, a calculation may be performed by the control apparatus or by the human operator (hereafter an automated control apparatus will be assumed, although the processes may be performed manually under the control of a human operator who either physically controls the valves and switches driving force to the pump for times calculated by the operator) to determine how much solvent or diluent to pump into the cup 12 to get the desired concentration. The control/user interface system 98 (hereafter the control system) then sends the proper control signals to switch the proper valves to the proper states to pump the selected solvent or solvents into the cup and sends the proper control signals to turn on the pump 84 and cause it to pump in the proper direction to deliver the calculated amount of solvent into the cup 12. For example, if solvent number 1 is to be used, control signals would be generated to open valve 130 and to open either valve 118 or valve 114 depending upon whether the walls were to washed down or not. The proper control signals to activate the pump 84 would then be generated to cause the pump to pump solvent from the port 132, through the manifold 96 and the pipe 88 through the pump 84 and the pipe 86, through the manifold 94 and out into the cup 12 through either the nozzle 28 or the fill pipe 26. These control signals to the pump are such as to cause the necessary volume of solvent to achieve the desired concentration to be pumped into the cup 12.

After the solvent is pumped in, the mixer/grinder 30A may be turned on to mix the solvent and the powder or solid chunks to dissolve the solids. Of course with granulated or powder samples the above noted step of turning on the mixer/grinder 30A before pumping in the solvent may be eliminated. In such embodiments, the solvent may be pumped in as soon as the cup is attached to the lid, and then the mixer/grinder 30A may be turned on to dissolve the sample.

Once the sample is dissolved, if the proper concentration of solvent is present and the solution is homogeneous, the control system forces a predetermined volume of the diluted sample to be pumped to the LC system. To do this the control system 98 causes valves 124, 102 and 114 to be opened and valve 145 in the effluent line to be closed. The valve 146 is caused to couple the portion 160 of the effluent line to the portion 144 of same and pipe 148 is closed off by the valve 146. The result of all these valve operations is than pressurized gas from the pressure source 104 pressurizes the sample preparation chamber defined by the cup 12 and the cap 14 via the manifold 94 and the fill pipe 26. The seals 16 prevent the pressurized gas from leaking away. The pressure forces the liquified sample in the chamber to enter the portion 160 of the effluent line and pass through the valve 146 to the portion 144 of the effluent line. Because the valve 145 is closed, the sample enters the pipe 162 and passes through the manifold 96 where it passes through the valve 124, pipe 164 and filter 126 and is forced through the liquid chromatography analyzer 128.

The problem with this approach is that it is not known how much liquid has been pumped. Generally, it is desirable to pump between 4 to 6 times the volume of the connecting tubings (as a minimum) through the system to flush out the lines and to fill the "loop" in the valve in the LC system 128. It is preferred because of timing considerations to know exactly when the sample loop is filled up so that the timing of examination of the output may be established.

If the proper concentration for the sample was not present after the solvent was pumped in, the sample metering valve may be operated as described above by the control system to take a known volume of sample and isolate it. Then the control system causes the three way valve 146 to couple pipe 160 to pipe 144 and valve 145 to open. Then, the valves 102 and 114 are opened, and the remaining sample is flushed through the effluent line 160 to waste by the pressurized gas. Next, if desired, the walls may be washed down by opening one of valves 130, 134 or 138 and the valves 92, 90 and 118 and activating the pump to pump some user defined or fixed quantity of a solvent or solvents through the nozzle 28 to wash down the walls. The mixer/grinder 30A which may a variable speed motor 30 in the preferred embodiment, may be turned on at a high speed during or after the sprinkling process to create turbulence to more thoroughly clean the walls. After the excess sample and solvent are cleaned off the walls, the waste solvent and sample in the cup 12 may be driven to waste by use of the pressurized gas source 104 as defined above. Thereafter, the control system operates the sample metering valve to release the isolated sample back into the cup 12, and operates the pump 84 to pump a calculated amount of solvent into the cup to achieve the user defined concentration for the diluted sample. The manner of doing these operations is as defined above.

Once the desired sample concentration is reached, and the liquid in the cup is homogeneous, the system is ready to have the diluted sample pumped through the LC system. To do this, the pressurized gas method defined above can be used, but the preferred embodiment of getting the liquid sample out of the sample chamber, regardless of whether it was originally two phase liquid/solid, two phase liquid/liquid, solid or extremely viscous is to pump the diluted sample out using the pump 84. The reason this pumped method is preferred is that the system is less complicated from a timing standpoint. With a known volume system, it is known how many pump strokes are necessary to move liquid from the sample cup 12 to the LC system 128. Thus the time to get the sample to the LC system is known, and the control system can control the LC system based upon this known time. If the pressurized gas method is used, the time it takes the liquid sample to get from the sample cup to the LC system is not known because of the the unknowns of the viscosity of the diluted sample changing from one sample to the next, and any tubing or fitting changes may also alter the timing. To control such a system, there would have to be an interrupt generated to the control processor or control system when the LC system 128 received the required amount of sample and is ready to go. A polled system would also work. These timing considerations, although not terribly complicated, are additional functions the control system must perform.

To pump the sample to the LC system 128 using the pump 84, the valves 114, 90, 92 and 124 are opened, and the pump is energized to pump from 4 to 6 times the tubing volume, typically 10 to 30 milliliters of diluted sample, to the fill pipe 26, manifold 94, pipe 86, pipe 88 and manifold 96 and pipe 164 as the pathway. This provides better control of the volume of sample delivery to the LC system so that the control of the LC analysis system 128 needs no interrupt or polling to indicate when the sample has arrived. To perform the above steps however requires that the amount of solvent/diluent pumped into the sample preparation chamber be such as to bring the liquid level of the diluted sample at the final concentration to a level above the end of the fill pipe 26. To avoid such complications, it is preferred to put the end 166 of the fill pipe 26 close to the bottom 168 of the sample preparation chamber. This eliminates the need for tradeoffs regarding the volume of the isolation chamber and the volumes of solvent/diluent to pump in to make sure that at all volumes of samples, the final liquid level after dilution will be above the level of the end 166 of the fill pipe 26. In the preferred embodiment, the level of the end 166 of the fill pipe 26 may be manually or automatically adjusted to account for such variations. This provides the extra facility of being able to keep the end 166 of the fill pipe off the bottom for samples which have sediment or solid material therein which could plug the fill pipe 26 if they were sucked up into the fill pipe.

Sample Dilution Without The Use of a Sample Metering Valve

Figures 10, 11:
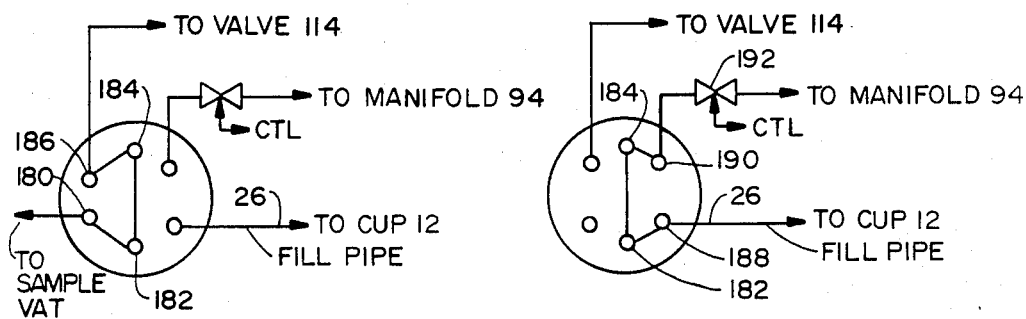
FIG. 10 is a symbolic diagram of a 6 way valve in a first state which may be used to replace the sample metering valve for certain types of samples.
FIG. 11 is a symbolic diagram of the 6 way valve of FIG. 10 in a second state.

The sample preparation process where clean, homogeneous samples are to be analyzed, there is no need for the step of homogenization. In such a situation, a 6 way valve may be used to introduce the sample to the cup 12. This valve may be used to isolate a known volume of sample in a loop between valve ports 182 and 184. FIGS. 10 and 11 illustrate how this can be done using two states of a 6 way valve. In FIG. 10 the 6 way valve is shown in the state in which the sample may be drawn from the sample vat. In this state, port 180 is connected to the sample vat and is also connected to port 182. Port 182 is always coupled to port 184 by an internal or external passageway regardless of the state of the valve. It is this passageway which will be used as the isolation chamber in place of the sample isolation chamber in the sample metering valve. The port 186 is coupled to the port 184 in this first state, and is also coupled to the manifold 94 through the valve 114. While the 6 way valve is in the state shown in FIG. 10, the control system 98 opens the valves 114, 90, 92, 142 and 145 and operates the pump to apply suction to the port 186. This draws sample up from the sample vat and fills the loop between ports 182 and 184 with sample. The pumping need only be long enough that the entire passageway between ports 182 and 184 is filled. Alternatively, the sample loop between ports 182 and 184 while the valve is in the state indicated by FIG. 10 may be filled manually by attaching a syringe filled with sample, or any device capable of forcing flow through the sample loop, to port 180 and forcing sample into the sample loop. Port 186 could then be simply connected to any waste receptacle.

The control system then switches the 6 way valve to the state shown in FIG. 11. In this state, the ports 182 and 184 are coupled, respectively, to ports 188 and 190. The port 190 is coupled to the manifold 94 by an additional solenoid or pneumatically operated valve 192, and the port 188 is coupled to the cup 12 via the fill pipe 26. When the 6 way valve is operated by the control system to put it in the state shown in FIG. 11, the sample that filled the passageway between the ports 182 and 184 is isolated. The control system then opens the valves 192, 90, 92 and one of the solvent valves 130 or 134 or 138 and operates the pump 84 to pump a known volume of solvent into the cup 12. The known volume of solvent is computed based upon the known volume of the passageway between the ports 182 and 184. The isolated sample and the known volume of solvent are then mixed by turning on the mixer/grinder 30. Thereafter, the diluted sample may be transferred to the analyzer 128 in any of the manners described above. In alternative embodiments, the ports 180 and 186 may be connected to a sample line with its own pump to fill up the passageway between the ports 182 and 184. The ports 188 and 190 in these embodiments are coupled, respectively, to the fill pipe 26 and to the manifold 94, and the valve 192 is not needed.

Preparing Samples Taken From a Process Stream

Figure 3:
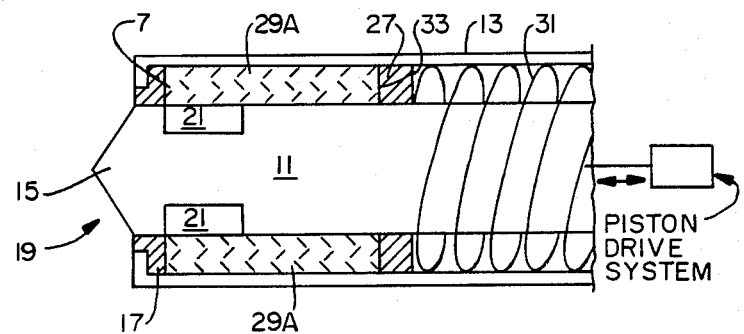
FIG. 3 is a cross sectional view of the sample metering valve of FIG. 2 with the piston retracted so as to isolate the sample.

The system according to the teachings of the invention is capable of isolating known volumes of samples from a process stream and preparing same for the analyzer. The valve 122 in FIG. 1 is used for this purpose. Control system 98 implements the process by causing the valve 122 to extract and isolate a known volume of sample flowing in process stream 192. The valve 122 is preferably an ISOLOK TM valve series M$ manufactured by Bristol Engineering of Yorkville, Illinois or equivalent. This valve is similar in operation to the valve shown in FIGS. 2 and 3 except that the there are additional ports in the cylinder of the valve coupled to the pipes 194 and 196. These ports are placed on the cylinder of the ISOLOK valve such that when the piston of the valve is in the retracted position, the isolation chamber of the ISOLOK valve analogous to the chamber 21 in FIGS. 2 and 3 is in a position such that pressurized gas or liquid in the pipe 194 will sweep the isolation chamber clear of sample and drive it into pipe 196 or vice versa.

To sample a process stream then, the valve 122 is operated by the control system 98 to isolate an aliquot of sample from the process stream 192. Then, the valves 92, 90, 120 and one of the solvent valves are opened. In addition, the valve 145 is closed, and the three way valve 146 is operated to couple the pipe 148 to the pipe 160. The pump 84 is then operated to draw a calculated amount of solvent from the solvent source and drive it through the pipe 194, the ISOLOK valve 122 and the pipe 196 to sweep the isolated sample out of the isolation chamber and into the cup 12 through the valve 146 and the effluent line 160. The amount of solvent drawn by the pump 84 is calculated from the desired final concentration and the known volume from the ISOLOK valve. Although the exact volume from the ISOLOK valve will not be known to the same precision as would the volume in the isolation chamber of the sample metering valve because of unknown dead volumes in the sealing rings, the precision is good enough for most applications.

Next, the mixer/grinder 30 is activated to homogenize the sample, and the liquid is then driven to the analyzer 128 for analysis in the manner described above.

Processing Slurry Samples

Slurry and other types of samples sometimes have gas bubbles entrained in the liquids. Gas bubbles may be at least partially drawn off before sample aliquot isolation in the system of FIG. 1 by the application of vacuum to the sample preparation chamber before operating the sample metering valve. The lower than atmospheric pressure causes outgassing of the gas entrained in the slurry or in foam bubbles on top of the liquid. Application of the vacuum is performed by the control system 98 by opening the valves 102 and 114 after the slurry is placed in the cup 12 in any of the processes described above. After the gases are drawn completely or substantially off, the sample metering valve 36 is operated to draw in an aliquot of slurry and to compress it as described above. After compression, a known volume of the compressed slurry is isolated, and the remaining slurry is transferred to waste as described above. The walls of the sample preparation chamber may also be washed down as described above if desired. Finally, the sample metering valve 36 is operated to release the isolated sample aliquot, and a known volume of solvent is pumped in as described earlier to arrive at the final concentration (serial dilution is possible in this process as it is in any of the processes described herein). The mixer/grinder 30 is then turned on by the control system 98, and the required amount of the diluted sample is transferred to the analyzer 128 as described above.

The water supply 112 may be used to flush out all the pipes in the system by properly operating the valves, but its principal use is in flushing out the sample preparation chamber.

Figure 12:
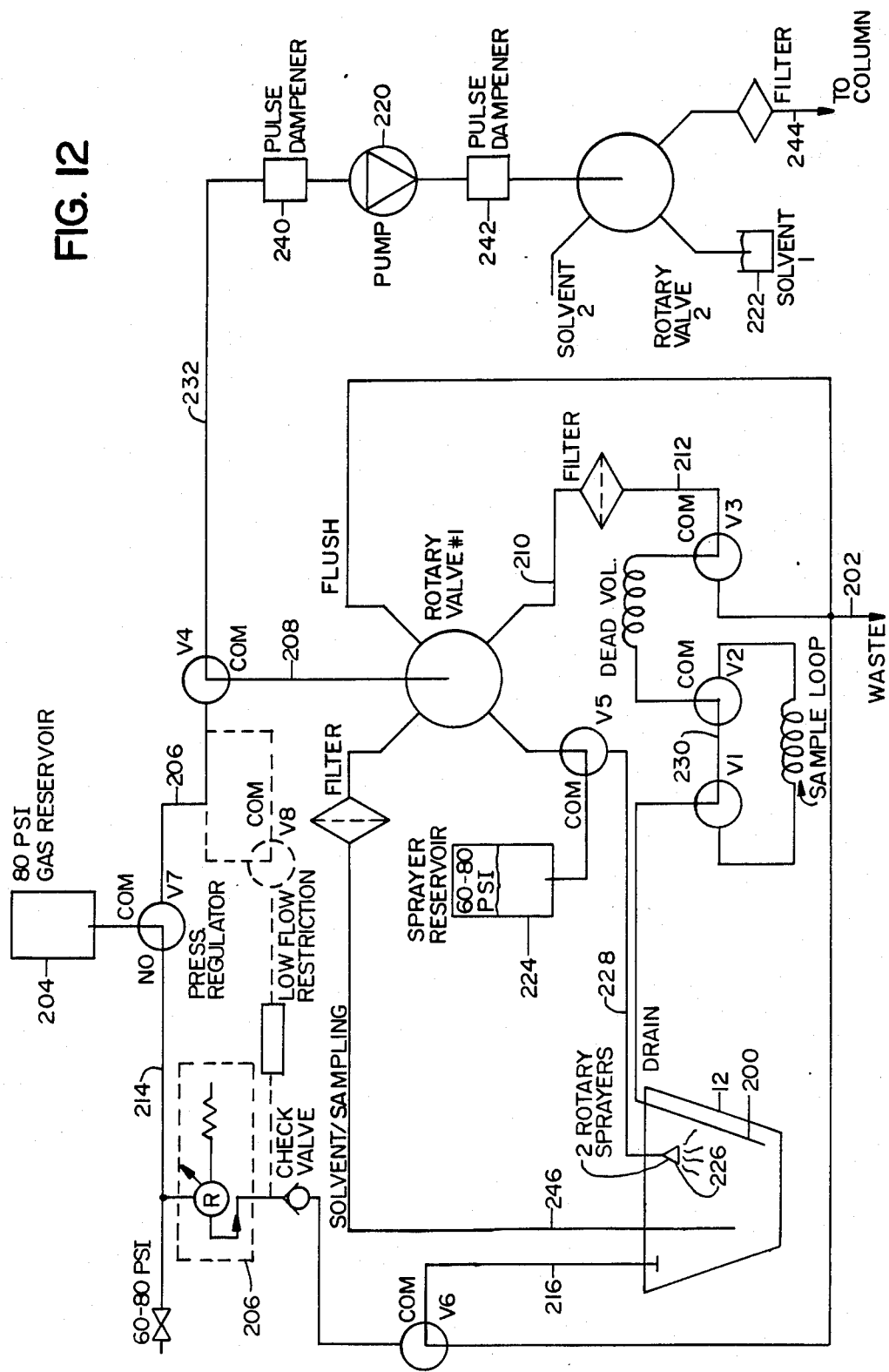
FIG. 12 is a diagram of an alternative embodiment of the basic invention where the collection of valves constituting the two manifolds in FIG. 1 are replaced in part by multiport rotary valves.

Referring to FIG. 12 there is shown a diagram of another embodiment of the sample preparation system of the invention. In this embodiment, the sample valve is comprised of the three way valves V1, V2 and V3 which operate in the manner described with respect to FIG. 9. Further, the manifolds 94 and 96 are replaced by rotary valves 1 and 2. All the valves are controlled by a control system (not shown) which causes the valves to operated in the proper sequence as described below. To take a sample in the system of FIG. 12, the cup 12 is filled with sample, and valves V1, V2 and V3 are operated to gate the drain line 200 to waste line 202 through the sample loop and the dead volume. The sample is driven to waste by pressurizing the cup via proper operation of V7 to pressurize the gas reservoir 204 with gas and then to use the gas reservoir pressure to pressurize the cup through the valves V7, V6 and the pressure regulator 206.

After the sample loop has been filled, valves V1 and V2 are operated to isolate the sample loop, and V7, V4 and rotary valve 1 are operated to pressurize lines 206, 208, 210, 212 and 200 to drive remaining sample back into the cup. Then the remaining sample in the cup is driven to waste by changing valve V3 to direct flow through drain line 200 to the waste line 202 and the cup is again pressurized using the gas reservoir 204, valves V7 and V6, pressure regulator 206 and the lines 214 and 216. This forces all the sample out of the cup.

The cup is then rinsed by operating rotary valves 1 and 2 and valves V4 and V5 and pump 220 to pump solvent from reservoir 222 into the sprayer reservoir 224. The sprayer reservoir is then pressurized by operating valves V7, V4, and V5 and rotary valve 1 so that pressurized gas is directed from gas reservoir 204 into the sprayer reservoir. The cup is then washed by operating valve V5 so as to direct the solvent in the sprayer reservoir 224 through the rotary sprayers 226 via line 228. The rotary sprayer directs the pressurized solvent stream around inside the cup to wash down all the internal structures by solvent impact. The cup is then emptied of solvent by pressurizing the cup in the manner described above and operating valves V1, V2 and V3 so that the solvent is directed through pipe 230 and the dead volume out through the waste pipe 202.

The fixed volume of sample trapped in the sample loop is then driven back into the cup by operating the pump 220 and rotary valves 1 and 2 to suck a desired diluent/solvent from a reservoir 222 (or other solvents in other reservoirs coupled to rotary valve 2 could be used) and pump it through pipe 232, valve V4, pipes 208 and 210 and 212, the dead volume, the sample loop and the drain pipe 200. The pump 220 is driven to pump a known volume of the selected solvent into the cup thereby pushing the known volume of sample in front of the pumped solvent into the cup along with a known amount of solvent. Pulse dampeners 240 and 242 remove any pulses from all pumping actions done by the system to minimize or eliminate any cavitation and bubbles from the system. As was the case when the sample was first introduced into the cup, a homogenizer or ultrasonic mixer or any other type of stirrer (not shown) may be used to mix the sample, homogenize it or mix it thoroughly.

Having reduced the sample aliquot to the proper concentration, the system is now ready to be pumped through the chromatography system. This is done by operating valves V1, V2, V3 and V4 and rotary valves 1 and 2 such that a path is established from the drain pipe 200 through the pump 220 and out pipe 244 to the chromatography system for assay. If it is desired to sample from a higher layer, the pipe 246 may be used by properly operating the valves in the system to use pipe 246 as the input path to the pump 220. The pipes in the system which still have sample in them and the cup may be purged with solvent in a manner which will be apparent to those skilled in the art from the above discussion.

Another manner of using the system of FIG. 12 is to put a liquid sample containing a chemical of interest in solution in the cup. The pump and valves may then be operated to pump a known volume of the sample through the liquid chromatography column to concentrate the chemical of interest on the active agent which coats the packing material of the column.

Although the invention has been described in terms of the preferred and alternative embodiments detailed herein, other alternative embodiments may be apparent to those skilled in the art. All such alternative embodiments which appropriate the spirit of the invention are intended to be included within the scope of the claims appended hereto.

What is claimed is:

1. A process of preparing a sample of a substance for chemical assay comprising the steps of:
   (a) automatically rendering the sample suitable for dilution in a solvent;
   (b) pressurizing the sample by means of a pressure source to compress any gas bubbles in the sample and to produce a known volume of sample;
   (c) diluting the known volume of sample to a predetermined sample concentration to form a diluted sample;
   (d) homogenizing the diluted sample; and
   (e) delivering the homogenized diluted sample to a chemical assay system.

2. A process of preparing a sample of a substance for chemical assay comprising the steps of:
   (a) automatically rendering the sample suitable for dilution in a solvent;

(b) isolating a portion of the sample in a sample metering valve coupled to a pressure source;

(c) pressurizing the portion of the sample in the sample metering valve by means of the a pressure source to compress any gas bubbles in the portion of the sample and to produce a known volume of sample;

(d) diluting the known volume of sample to a predetermined sample concentration to form a diluted sample;

(e) homogenizing the diluted sample; and (f) delivering the homogenized diluted sample to a chemical assay system.

3. A process for preparing a sample for assay comprising the steps of:

(a) operating a sample valve so as to extract a first volume of a sample from a sample preparation chamber;

(b) compressing the first volume of sample so as to compress any gas therein to a small volume and to thereby form a known volume of sample from the first volume of sample;

(c) removing any of said sample remaining in the sample preparation chamber from the sample preparation chamber;

(d) driving the known volume of sample out of the sampling valve back into the sample preparation chamber;

(e) placing a predetermined amount of diluent in the sample preparation chamber;

(f) homogenizing the known volume of sample and the diluent in the sample preparation chamber to form a diluted sample; and (g) delivering the diluted sample to an assay system.

4. The process of claim 3 which further comprises the steps of:

(h) isolating a known volume of the diluted sample from the sample preparation chamber after the homogenizing step and before the delivering step to obtain a non-isolated volume of diluted sample in the sample preparation chamber and an isolated volume of diluted sample which is isolated from the sample preparation chamber;

(i) flushing the non-isolated volume of diluted sample from the sample preparation chamber to waste;

(j) adding another predetermined amount of a diluent to the sample preparation chamber;

(k) releasing the isolated volume of diluted sample back into the sample preparation chamber to form a further diluted sample;

(l) homogenizing the further diluted sample to form a homogenized, further diluted sample; and (m) repeating steps (h)-(l) utilizing the homogenized further diluted sample until a predetermined sample concentration is achieved.

5. A process for preparing a sample having gas bubbles entrained therein or foam on a surface thereof comprising the steps of:

(a) placing said sample into a sample preparation chamber;

(b) drawing a portion of said sample from said sample preparation chamber into a sample metering valve;

(c) compressing the portion of said sample drawn into said sample metering valve;

(d) isolating a known volume of the compressed sample in said sample metering valve;

(e) removing any of said sample remaining in the sample preparation chamber from the sample preparation chamber;

(f) releasing the isolated known volume of compressed sample into the sample preparation chamber and adding an amount of diluent to said isolated volume of compressed sample in said sample preparation chamber to form a diluted sample;

(g) homogenizing said diluted sample in said sample preparation chamber to form a homogenized, diluted sample;

(h) repeating steps (b)-(g) utilizing said homogenized, diluted sample until a predetermined sample concentration is reached; and (i) delivering the homogenized, diluted sample to an assay system.

6. The process of claim 5 wherein the step of compressing the portion of sample drawn into said sample metering valve is done by applying pressurized gas to said portion of sample drawn into said sample metering valve.

7. The process of claim 5 wherein the sample metering valve includes a compression chamber, an isolation valve, and a piston, and wherein steps (b)-(d) are carried out by drawing said portion of sample into said compression chamber through said isolation valve by drawing said piston up to increase the volume of the compression chamber, closing the isolation valve, and moving the piston to decrease the volume of the compression chamber until a predetermined criterion is reached and determining the amount of decrease in volume which occurred because of movement of the piston until said predetermined criterion is reached.

8. A process for preparing a sample for assay comprising the steps of:

(a) placing a non-homogeneous sample into a sample preparation chamber;

(b) homogenizing said non-homogeneous sample with a stirrer, thereby generating a homogenized sample;

(c) aspirating a quantity of said homogenized sample into a sample metering valve which has a chamber of known volume and which is coupled to a means for pressurizing said aspirated quantity of homogenized sample, thereby generating an aspirated, homogenized sample;

(d) pressurizing said aspirated, homogenized sample in said sample metering valve to compress any gas bubbles in said aspirated, homogenized sample, thereby generating a pressurized, homogenized sample;

(e) isolating a known volume of said pressurized, homogenized sample in said chamber of known volume in said sample metering valve to obtain a non-isolated volume of sample in the sample preparation chamber and an isolated quantity of said pressurized, homogenized sample of known volume which is isolated from the sample preparation chamber;

(f) flushing said non-isolated volume of sample from the sample preparation chamber to waste;

(g) releasing the isolated quantity of said pressurized, homogenized sample of known volume back into the sample preparation chamber;

(h) placing a predetermined amount of a diluent into the sample preparation chamber to form a diluted sample from said isolated quantity of said pressurized, homogenized sample of known volume;

(i) homogenizing said diluted sample in said sample preparation chamber, thereby generating a homogenized, diluted sample;

(j) repeating steps (c)–(i) utilizing said homogenized, diluted sample until a predetermined sample concentration is reached; and (l) delivering a predetermined volume of the homogenized, diluted sample to an assay device.

9. A process for preparing a sample for assay comprising the steps of:

(a) operating a sample valve so as to extract a first volume of a sample from a sample preparation chamber, wherein said sample valve includes a main tube and a secondary tube, the secondary tube being connected to the main tube via a first valve at a first junction and via a second valve at a second junction, and wherein a pressure source is coupled to the main tube, and wherein the first volume of sample is isolated from the sample preparation chamber by operating the first and second valves and the pressure source so as to drive the first volume of sample into the secondary tube;

(b) forming a known volume of sample from the first volume of sample;

(c) removing any of said sample remaining in the sample preparation chamber from the sample preparation chamber;

(d) driving the known volume of sample out of the secondary tube back into the sample preparation chamber;

(e) placing a predetermined amount of diluent in the sample preparation chamber;

(f) homogenizing the known volume of sample and the diluent in the sample preparation chamber to form a diluted sample; and (g) delivering the diluted sample to an assay system.

10. The process of claim 9 wherein the step of forming the known volume of sample from the first volume of sample comprises compressing the first volume of sample within the secondary tube by operating the first and second valves and the pressure source so as to compress any gas in the first volume of sample to a small volume.

11. The process of claim 9 which further comprises the steps of:

isolating a known volume of the diluted sample from the sample preparation chamber after the homogenizing step and before the delivering step to obtain a non-isolated volume of diluted sample in the sample preparation chamber and an isolated volume of diluted sample which is isolated from the sample preparation chamber;

(i) flushing the non-isolated volume of diluted sample from the sample preparation chamber to waste;

(j) adding another predetermined amount of a diluent to the sample preparation chamber;

(k) releasing the isolated volume of diluted sample back into the sample preparation chamber to form a further diluted sample;

(l) homogenizing the further diluted sample to form a homogenized, further diluted sample; and (m) repeating steps (h)–(l) utilizing said homogenized further diluted sample until a predetermined sample concentration is achieved.

12. A process for preparing a sample for assay comprising the steps of:

(a) placing said sample into a sample preparation chamber having walls;

(b) drawing a portion of said sample from said sample preparation chamber;

(c) compressing the portion of said sample drawn from said sample preparation chamber;

(d) isolating a known volume of the compressed sample;

(e) removing any of said sample remaining in the sample preparation chamber from the sample preparation chamber to waste;

(f) spraying a solvent against the walls of said sample preparation chamber;

(g) flushing the sprayed solvent to waste;

(h) releasing the isolated known volume of compressed sample into the sample preparation chamber and adding an amount of diluent to said isolated volume of compressed sample in said sample preparation chamber to form a diluted sample;

(i) homogenizing said diluted sample in said sample preparation chamber to form a homogenized diluted sample;

(j) repeating steps (b)–(i) utilizing the homogenized diluted sample until a predetermined sample concentration is reached; and (k) delivering the homogenized, diluted sample to an assay system.

13. The process of claim 12 wherein the step of spraying a solvent on the walls of the sample preparation chamber includes the step of pumping the solvent through a nozzle in said sample preparation chamber that causes the solvent to be thrown against the walls of said sample preparation chamber.

14. A process for preparing a sample for assay comprising the steps of:

(a) filling a passageway of known volume in a six way valve with a sample, wherein said passageway is common to at least two switching states of said six way valve, said filling occurring while said six way valve is in one of said two states;

(b) switching said six way valve to the other of the two states;

(c) driving said sample from said common passageway into a sample preparation chamber;

(d) drawing a portion of said sample from said sample preparation chamber;

(e) compressing the portion of said sample drawn from said sample preparation chamber;

(f) isolating a known volume of the compressed sample;

(g) removing any of said sample remaining in the sample preparation chamber from the sample preparation chamber;

(h) releasing the isolated known volume of compressed sample into the sample preparation chamber and adding an amount of a diluent to said isolated volume of compressed sample in said sample preparation chamber to form a diluted sample;

(i) homogenizing said diluted sample in said sample preparation chamber to form a homogenized, diluted sample;

(j) repeating steps (d)–(i) utilizing said homogenized, diluted sample until a predetermined sample concentration is reached; and (k) delivering the homogenized, diluted sample to an assay system.

* * * * *